(12) United States Patent
Nishino et al.

(10) Patent No.: US 8,172,290 B2
(45) Date of Patent: May 8, 2012

(54) GRIPPER

(75) Inventors: Yukinobu Nishino, Kanazawa (JP);
Tokuo Nishi, Kanazawa (JP); Yukihiro Yamamoto, Kanazawa (JP)

(73) Assignee: Shibuya Kogyo Co., Ltd., Kanazawa-Shi, Ishikawa (JP)

( * ) Notice: Subject to any disclaimer, the term of this patent is extended or adjusted under 35 U.S.C. 154(b) by 281 days.

(21) Appl. No.: 12/449,239

(22) PCT Filed: Jan. 18, 2008

(86) PCT No.: PCT/JP2008/050615
§ 371 (c)(1),
(2), (4) Date: Nov. 13, 2009

(87) PCT Pub. No.: WO2008/093548
PCT Pub. Date: Aug. 7, 2008

(65) Prior Publication Data
US 2010/0061831 A1 Mar. 11, 2010

(30) Foreign Application Priority Data

Jan. 31, 2007 (JP) .................. 2007-020912
Nov. 15, 2007 (JP) .................. 2007-297118

(51) Int. Cl.
*B65G 47/90* (2006.01)
*B25J 15/00* (2006.01)
(52) U.S. Cl. .............. 294/99.1; 294/902; 198/803.7
(58) Field of Classification Search .............. 294/33, 294/87.2, 99.1, 902; 198/803.7, 803.8, 867.05, 198/867.06
See application file for complete search history.

(56) References Cited

U.S. PATENT DOCUMENTS

| 3,885,825 | A | * | 5/1975 | Amberg et al. ............ 294/115 |
| 4,022,363 | A | * | 5/1977 | Eliassen ................ 294/87.2 |
| 4,379,578 | A | * | 4/1983 | Schuler ................ 294/31.2 |
| 4,768,403 | A | * | 9/1988 | Bar-Noy ................ 81/3.15 |
| 4,941,699 | A | * | 7/1990 | Wilfong ............... 294/99.1 |
| 7,287,792 | B2 | * | 10/2007 | Tye ................... 294/103.1 |

FOREIGN PATENT DOCUMENTS

| JP | 1-261111 | 10/1989 |
| JP | 51-26870 | 5/1993 |
| JP | 2003-112713 | 4/2003 |
| JP | 2006-61558 | 9/2007 |

OTHER PUBLICATIONS

Japanese Patent Office Search Report dated Apr. 1, 2008 (2 pages).
Notification ot Transmittal of International Search Report (4 pages).
Written Opinion of International Searching Authority (3 pages).

* cited by examiner

*Primary Examiner* — Dean Kramer
(74) *Attorney, Agent, or Firm* — Flynn, Thiel, Boutell & Tanis, P.C.

(57) ABSTRACT

A gripper has a pair of supports 22A, 22B positioned on opposite sides of a bottle made of resin, and abutments 24A, 24B disposed respectively on the supports 22A, 22B for holding the bottle 4 made of resin, each of the abutments 24A, 24B have two thin plates 26A, 28A, 26B, 28B which are vertically spaced from each other. The abutments 24A, 24B hold the bottle 4 by gripping a neck 4a of the bottle 4 on its opposite sides. While holding the bottle 4, the supports 22A, 22B are held out of contact with an outer surface of the bottle 4, allowing the electron beam to travel around the neck 4a to sterilize the entire surface of the bottle 4.

6 Claims, 4 Drawing Sheets

[Fig. 1]
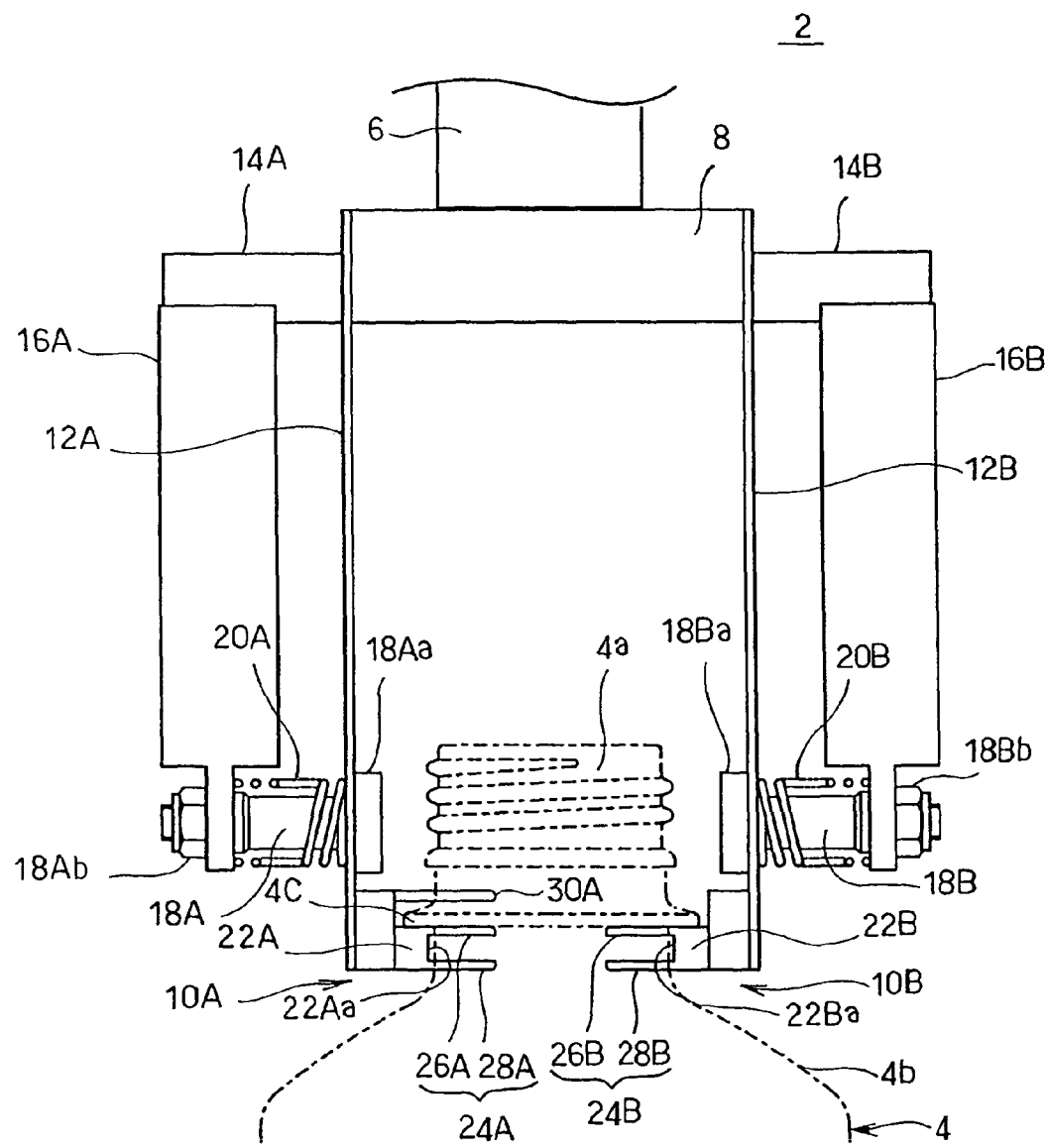

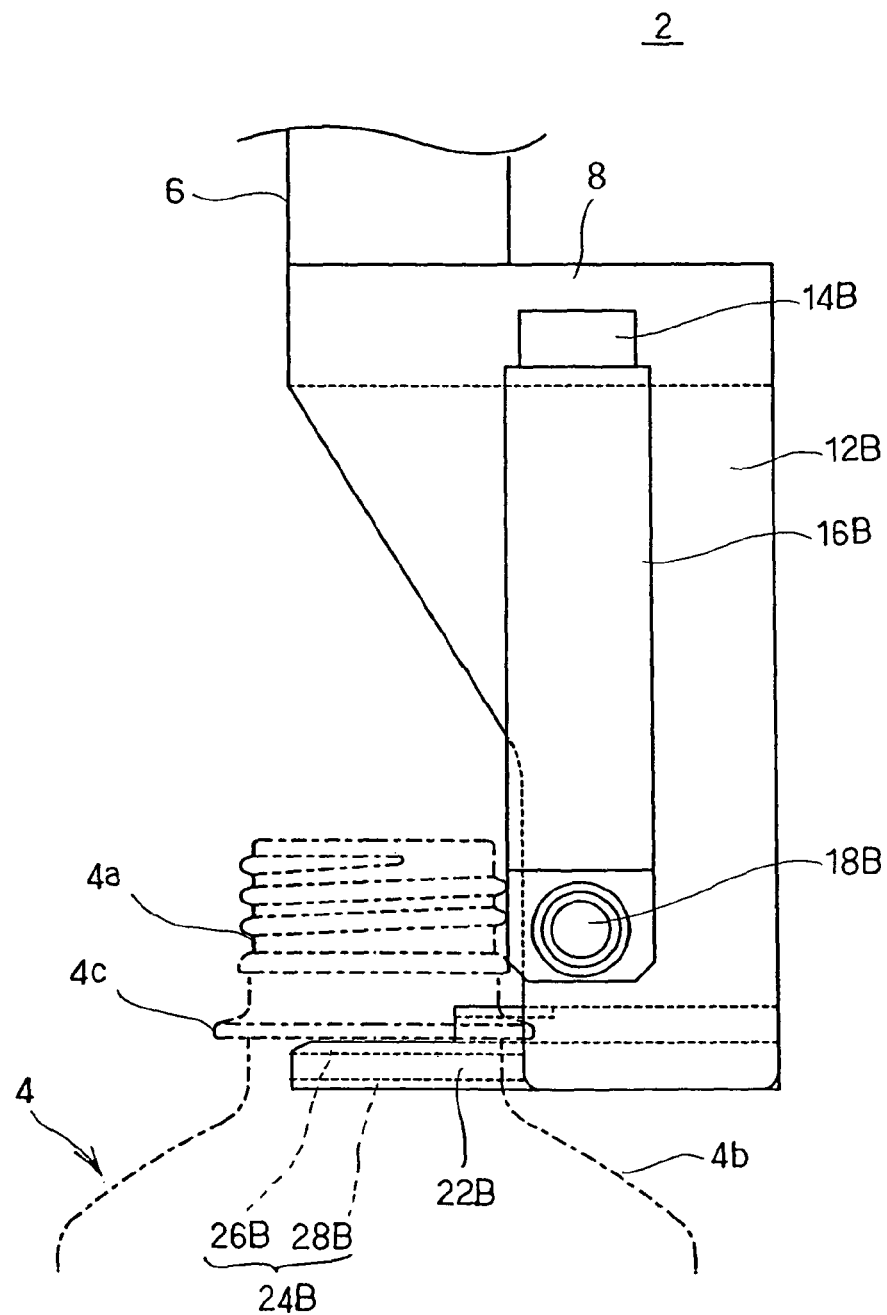
[Fig. 2]

[Fig. 3]
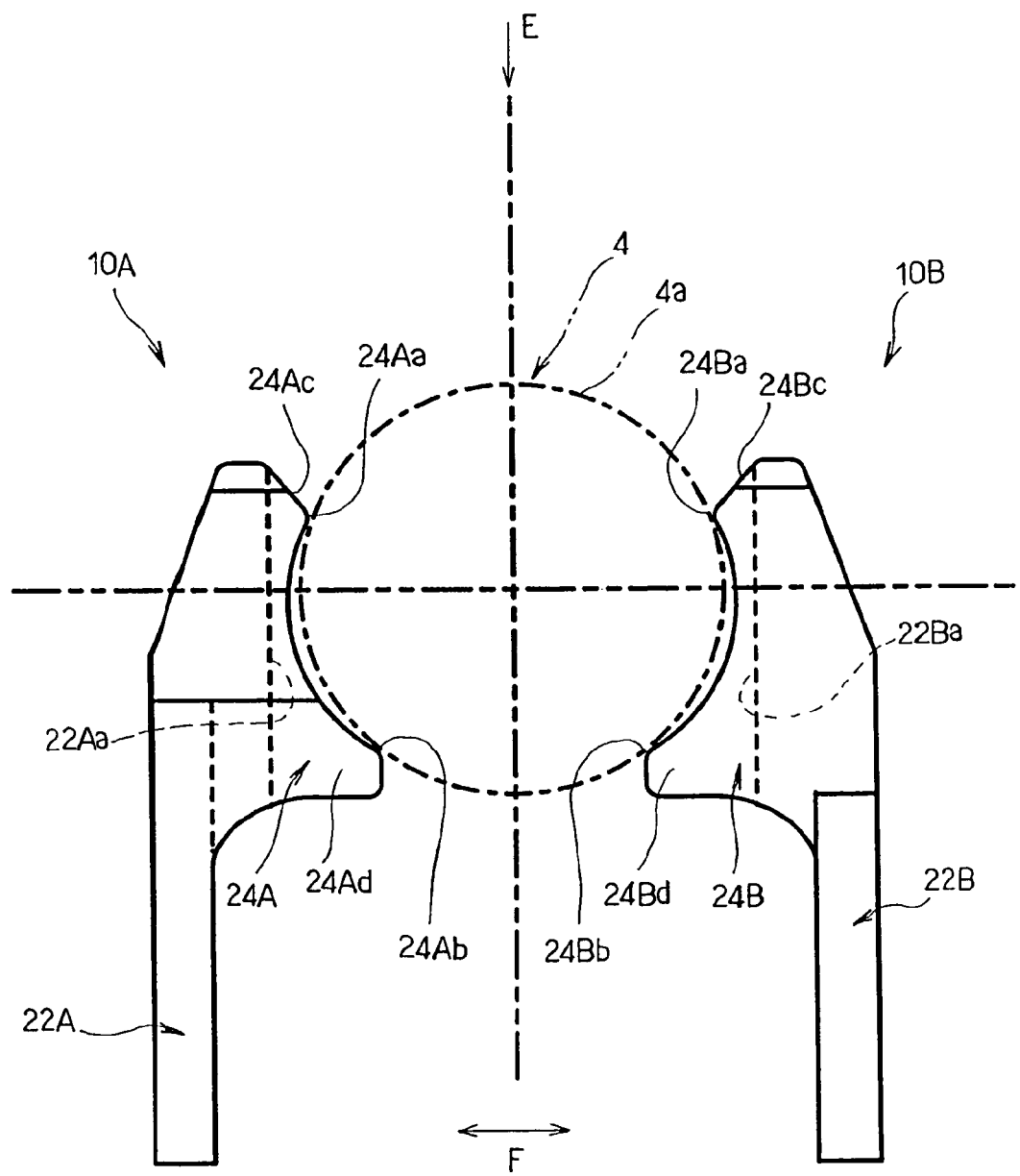

[Fig. 4]
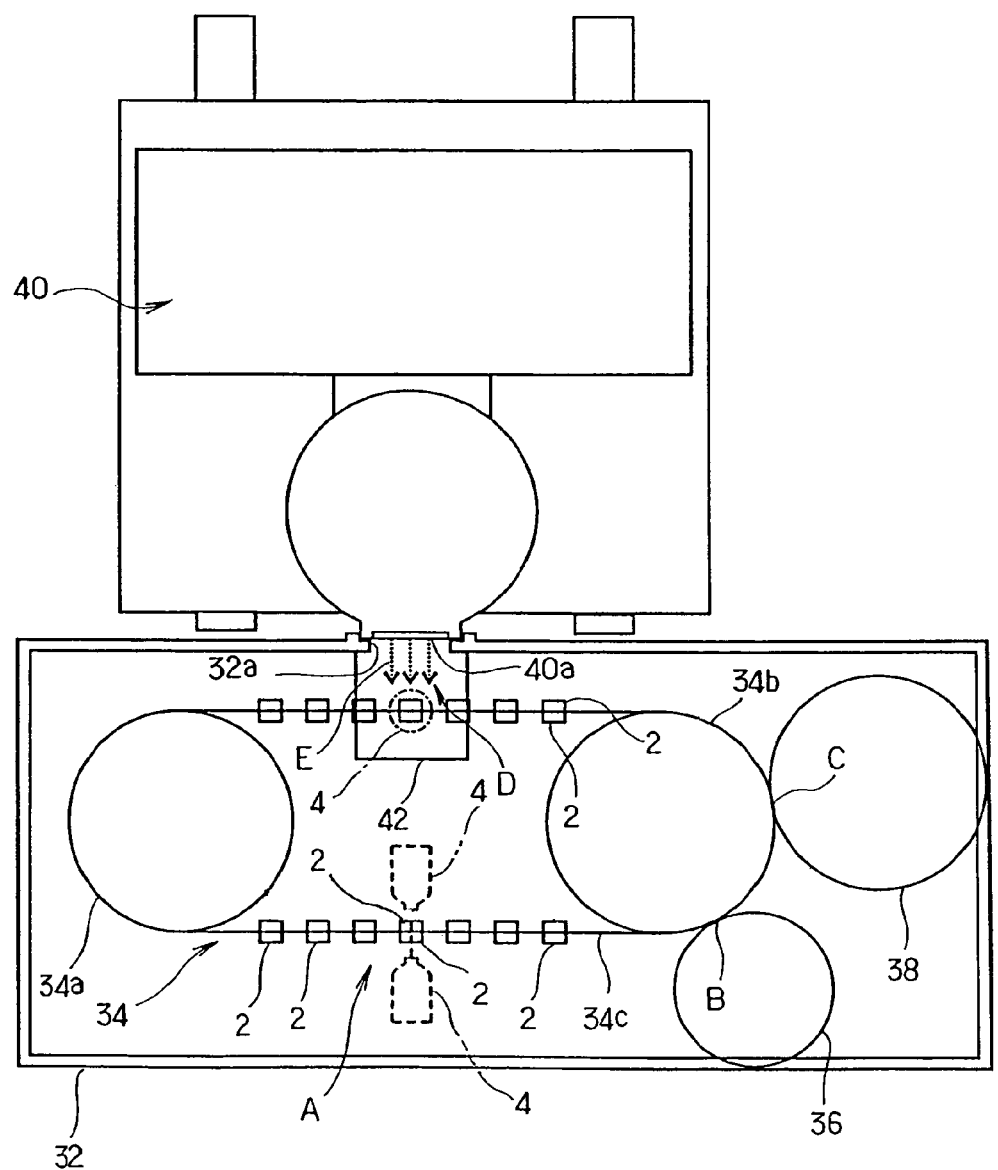

GRIPPER

TECHNICAL FIELD

The present invention relates to a gripper for holding the neck of a bottle made of resin by gripping the same on its opposite sides, and more particularly to a gripper for use in, for example, an electron beam sterilization apparatus for irradiating a vessel being fed by a feeding apparatus with an electron beam thereby to sterilize the vessel.

BACKGROUND ART

There have heretofore been known apparatus for sterilizing a vessel being fed by a feeding apparatus by irradiating the vessel with an electron beam from an electron beam irradiation apparatus (see, for example, Patent document 1, Patent document 2, and Patent document 3). Patent document 1 discloses a vessel feeding means having two parallel rails for slidingly suspending and supporting the neck directly below a flange on the outer circumferential surface of the mouth of a vessel such as a PET bottle or the like. The parallel rails are provided by a rail member having a recess defined therein in a range corresponding to the transverse width of an EB (electron beam) irradiation chamber. The recess is covered with a thin web of titanium film to make up for the interruption in the rails without obstructing the irradiation with the EB.

Patent document 2 discloses an invention relating to a feeding means having two wires which is disposed in an irradiation chamber. The two wires are moved to feed a vessel in an upright state.

Patent document 3 discloses a feed conveyor including a ring-shaped feed gear mounted on an inner circumferential surface thereof, support posts vertically mounted on the ring-shaped feed gear at given spaced intervals, and a ring-shaped guide ring mounted on the upper ends of the support posts. Neck guides are mounted on the guide ring at respective positions which correspond to the pitch intervals of vessels, whose necks are held by the neck guide while the vessels are fed by the feed conveyor.

There has also heretofore been known a gripper for holding the neck of a bottle made of resin by gripping the neck on its opposite sides, as disclosed in Patent document 4, though the gripper has nothing to do with an electron beam sterilization apparatus. The disclosed gripper has two arms with gripping teeth on respective ends thereof for holding the neck of a bottle by tightening the opposite sides thereof.

Patent document 1: Japanese Patent Application Laid-Open Publication No. 11-1212
Patent document 2: Japanese Patent Application Laid-Open Publication No. 1-19190
Patent document 3: Japanese Patent Application Laid-Open Publication No. 2000-214300
Patent document 4: Japanese Patent No. 3787328

DISCLOSURE OF THE INVENTION

Problems to be Solved by the Invention

The structures of the vessel feeding means disclosed in Patent document 1 and Patent document 2 have been problematic in that the intervals before and after vessels being fed and the speed at which the vessels are fed tend to become unstable, possibly resulting in fluctuations in the conditions under which the vessels are irradiated with the electron beams. The structure disclosed in Patent document 3 is disadvantageous in that the neck guides which are holding the vessels block the electron beam, preventing the electron beam from being sufficiently applied to the vessels in their entirety.

The gripper which is shaped as disclosed in Patent document 4 is capable of holding a vessel more stably if the gripping teeth have a wider surface for contact with the vessel. Therefore, as the thickness of the gripping teeth, i.e., the vertical height of their surfaces for contact with the vessel, is greater, the gripping teeth can hold the vessel more reliably and feed the vessel more stably. If the gripper is used as a feeding device in an electron beam irradiation apparatus, then the portion of the gripper which is held in contact with the vessel interrupts the electron beam. Consequently, if the area of the gripper which is held in contact with the vessel is large, then a problem arises in that the gripper prevents the vessel from being fully sterilized.

Means for Solving the Problems

According to the present invention, a gripper for holding the neck of a bottle made of resin by gripping the neck on its opposite sides, comprises a pair of supports positioned on opposite sides of the neck of the bottle made of resin, and abutments disposed respectively on the supports for abutting against an outer circumferential surface of the neck of the bottle to hold the neck, each of said abutments comprising a plurality of support bodies which are vertically spaced from each other.

According to invention, said support bodies comprise thin plates, respectively.

According to the invention, said supports are held out of contact with the outer circumferential surface of the neck of the bottle while holding the bottle made of resin.

According to the invention, at least one of said supports has a wobble stopper for preventing the bottle made of resin from wobbling.

According to the invention, said support bodies abut against a lower portion of a flange on the neck of the bottle made of resin, and said wobble stopper abuts against an upper portion of said flange.

According to the invention, said abutments abut against the neck of the bottle made of resin at a plurality of points which are spaced apart in a circumferential direction of the neck.

According to the invention, which is concerned with a gripper for feeding the bottle made of resin held thereby to an irradiation region of an electron beam irradiating means, when the gripper holds the bottle made of resin in said irradiation region, the gripper has such a posture that said supports face in a feeding direction which is perpendicular to the direction E in which the gripper is irradiated with an electron beam, and the support bodies of said abutments lie substantially parallel to the direction E in which the gripper is irradiated with the electron beam.

Advantages of the Invention

With the gripper according to the present invention, each of the abutments disposed on the supports that are positioned on the opposite sides of the neck of the bottle made of resin comprises support bodies which are vertically spaced from each other. Therefore, the gripper is capable of holding the bottle stably though its area of contact with the bottle is small.

BRIEF DESCRIPTION OF THE DRAWINGS

FIG. 1 is a front elevational view of a neck gripper (Embodiment 1);
FIG. 2 is a side elevational view of the neck gripper;

FIG. 3 is a plan view of grips of the neck gripper; and

FIG. 4 is a plan view showing an example of an application wherein neck grippers are used in an electron beam sterilization apparatus.

DESCRIPTION OF REFERENCE CHARACTERS 2 gripper
4 bottle made of resin
4a neck
22A support
22B support
24A abutment
24B abutment
26A support body (plate)
26B support body (plate)
28A support body (plate)
28B support body (plate)

BEST MODE FOR EMBODYING THE INVENTION

Supports disposed on the respective opposite sides of the neck of a bottle made of resin have respective abutments each having vertically spaced support members. This structure makes it possible to achieve an object of holding a vessel reliably and feeding the vessel stably and also to reduce an area of contact between a gripper and a vessel so as not to prevent the vessel from being irradiated with an electron beam.

Embodiment 1

The present invention will be described below based on an embodiment shown in the drawings. A gripper 2 according to the embodiment is used in an electron beam sterilization apparatus for sterilizing an object by irradiating the object with an electron beam. A bottle 4 which is held and fed by the gripper 2 is sterilized by being irradiated with an electron beam when the bottle 4 passes in front of an electron beam irradiating means. The bottle 4 which is held by the gripper 2 according to the present embodiment comprises a bottle made of a resin, such as a PET bottle or the like, and includes a flange 4c on the outer circumferential surface of a neck 4a (a small-diameter portion disposed above a slanted shoulder 4b and having a substantially constant diameter).

Neck grippers 2 are mounted at equal intervals on a rotary wheel or an endless feed belt or the like which travels circulatively. Each of the neck grippers 2 includes a pair of grips 10A, 10B for holding a bottle 4, disposed below a horizontal mount 8 fixed to the lower end of a vertical rod 6. A pair of leaf springs 12A, 12B have upper ends directed upwardly and secured to respective opposite end faces of the mount 8. The bottle 4 is held in a position directly below the vertical rod 6. As shown in FIG. 2, the leaf springs 12A, 12B include a lower portion having a slanted cut-out shape out of interference with the neck 4a of the bottle 4. Horizontal joint members 14A, 14B are fixed to the respective opposite sides of the horizontal mount 8 (outwardly of the leaf springs 12A, 12B). Vertical support members 16A, 16B which are directed downwardly are mounted respectively on the lower surfaces of the ends of the respective horizontal joint members 14A, 14B. The vertical support members 16A, 16B are disposed in overlapping relation to lower portions of the leaf springs 12A, 12B which are disposed in positions laterally spaced from the neck 4a of the bottle 4 (see FIG. 2).

The vertical support members 16A, 16B are slightly shorter than the leaf springs 12A, 12B and have respective lower ends on which inwardly extending horizontal pins 18A, 18B are mounted. The pins 18A, 18B extend respectively through the leaf springs 12A, 12B at positions that are slightly above the lower ends of the leaf springs 12A, 12B. Helical springs 20A, 20B are disposed around the pins 18A, 18B extending between the support members 16A, 16B and the leaf springs 12A, 12B for normally biasing the leaf springs 12A, 12B to move in directions toward each other. The pins 18A, 18B have respective portions 18Aa, 18Ba of an increased diameter on their tip ends that are positioned on the inner surfaces of the leaf springs 12A, 12B. The portions 18Aa, 18Ba of an increased diameter serve to positionally limit the leaf springs 12A, 12B that are biased by the springs 20A, 20B, normally holding the leaf springs 12A, 12B vertically parallel to the support members 16A, 16B. When the lower ends of the leaf springs 12A, 12B are pushed from their inner surfaces, they can move away from each other against the biasing forces of the springs 20A, 20B.

The grips 10A, 10B are mounted respectively on the inner surfaces (facing each other) of the lower ends of the leaf springs 12A, 12B. The grips 10A, 10B comprise respective paired supports 22A, 22B mounted respectively on the leaf springs 12A, 12B and extending horizontally and respective abutments 24A, 24B disposed on distal ends of the supports 22A, 22B (in this specification, portions comprising thin plates will be referred to as abutments 24A, 24B, and portions other than the abutments 24A, 24B as supports 22A, 22B). The supports 22A, 22B are disposed parallel to each other such that they have respective distal end portions (upper portions in FIG. 3) positioned on the opposite sides of the neck 4a of the bottle 4. The abutments 24A, 24B which abut against the opposite sides of the neck 4a of the bottle 4 to hold the bottle 4 are disposed on the inner surfaces of the supports 22A, 22B near their distal ends, i.e., on the surfaces which face each other. Each of the abutments 24A, 24B comprises two thin plates 26A, 28A, 26B, 28B which are vertically spaced from each other. In the present embodiment, the two thin plates 26A, 28A, 26B, 28B are essentially identical in shape to each other, and have arcuate surfaces on their sides for abutment against the neck 4a of the bottle 4.

The two upper and lower plates 26A, 28A, 26B, 28B on the distal end of each of the supports 22A, 22B have a thickness of about 1 mm, and are vertically spaced from each other by about 3 mm in the present embodiment. Therefore, the abutments 24A, 24B which include the two upper and lower thin plates 26A, 28A, 26B, 28B have a thickness of about 5 mm in their entirety. As the vertical spacing between the two upper and lower thin plates 26A, 28A, 26B, 28B is greater, they can hold the bottle 4 more stably. However, if the overall thickness of the abutments 24A, 24B (the distance between the upper surface of the upper plates 26A, 26B and the lower surface of the lower plates 28A, 28B) exceeds 5 mm, then they may not be able to neatly grip the portion of the bottle 4 beneath the flange 4c. The thickness of the abutments 24A, 24B should preferably be 5 mm or smaller. In the present embodiment, the portion of the bottle 4 which is beneath the flange 4c on the neck 4a is gripped by the gripper. However, the above dimension allows the gripper to grip the portion of the bottle 4 which is above the flange 4c.

The plates 26A, 28A, 26B, 28B are mounted on flat surfaces 22Aa, 22Ba of the supports 22A, 22B. When the abutments 24A, 24B are holding the bottle 4, the flat surfaces 22Aa, 22Ba are held out of contact with the bottle 4. When the flat surfaces 22Aa, 22Ba are closest to the bottle 4, they are spaced from the bottle 4 by a distance of about 0.5 mm.

Therefore, when the abutments 24A, 24B are holding the bottle 4, there is a clearance between the outer circumferential surface of the neck 4a that is held in contact with the abutments 24A, 24B and the front surfaces 22Aa, 22Ba of the supports 22A, 22B. Except for the portions of the abutments 24A, 24B which are held in abutment against the outer circumferential surface of the neck 4a of the bottle 4, there is nothing covering the outer surface of the bottle 4. Even when the gripper 2 is used in an electron beam sterilization apparatus, the gripper 2 does not block the electron beam emitted from the electron beam irradiating means, but allows the electron beam to pass between the plates 26A, 28A, 26B, 28B along the surfaces 22Aa, 22Ba of the supports 22A, 22B while traveling around the neck 4a.

The two upper and lower thin plates 26A, 28A, 26B, 28B of the abutments 24A, 24B have the arcuate surfaces for abutment against the neck 4a of the bottle 4. The arcuate surfaces have a curvature greater than the curvature of the outer circumferential surface of the neck 4a. Consequently, the abutments 24A, 24B have distal-end protrusions 24Aa, 24Ba (upper protrusions in FIG. 3) and proximal-end protrusions 24Ab, 24Bb (lower protrusions in FIG. 3), i.e., two points (four points of the upper and lower plates), which are spaced in the circumferential directions of the neck 4a and held in abutment against the neck 4a of the bottle 4, and other portions which are slightly spaced from the outer circumferential surface of the neck 4a. Alternatively, the curvature of the arcuate surfaces of the plates 26A, 28A, 26B, 28B may be substantially equal to the curvature of the outer circumferential surface of the neck 4a, so that there is substantially no clearance therebetween. In the present embodiment, the abutments 24A, 24B for abutment against the neck 4a of the bottle 4 comprise the two upper and lower thin plates 26A, 28A, 26B, 28B. However, the abutments 24A, 24B are not limited to plates, but may be of other shapes, e.g., support bodies such as small projections or the like for abutment against the neck 4a.

The distal ends of the abutments 24a, 24B have respective slanted inner surfaces 24Ac, 24Bc to keep their most distal ends widely spaced from each other. When the bottle 4 is pushed in from the front side (front the upper side in FIG. 3), the supports 22A, 22B with the abutments 24A, 24B mounted thereon are spaced away from each other while causing the leaf springs 12A, 12B and the springs 20A, 20B to flex, allowing the bottle 4 to be inserted between the abutments 24A, 24B. When the bottle 4 moves beyond the distal-end protrusions 24Aa, 24Ba of the abutments 24A, 24B (between the slanted surfaces 24Ac, 24Bc and the arcuate surfaces), the bottle 4 enters between the arcuate surfaces of the abutments 24A, 24B. Under the spring forces of the leaf springs 12A, 12B and the springs 20A, 20B, the supports 22A, 22B and the abutments 24A, 24B return toward each other into their original positions, gripping the neck 4a of the bottle 4 on its opposite sides. The abutments 24A, 24B have respective proximal-end extensions 24Ad, 24Bd on which the proximal-end protrusions 24Ab, 24Bb are disposed. The proximal-end extensions 24Ad, 24Bd extend toward each other, and the proximal-end protrusions 24Ab, 24Bb are positioned respectively inwardly of the distal-end protrusions 24Aa, 24Ba. The bottle 4 which has been pushed in from the distal-end side is prevented from moving forwardly by the protrusions 24Ab, 24Bb on the opposite sides, and stops between the arcuate surfaces of the abutments 24A, 24B whereupon it is held by the front and rear protrusions 24Aa, 24Ba, 24Ab, 24Bb.

One of the grips 10A, 10B (the left grip 10A in FIGS. 1 and 3) has a wobble stopper 30A disposed slightly above the abutment 24A for preventing the bottle 4 held and fed by the neck gripper 2 from wobbling while it is being fed. The wobble stopper 30A is positioned above the flange 4c when the portion of the bottle 4 below the flange 4c is held by the grips 10A, 10B. If the bottle 4 which is held is tilted while it is being fed, the wobble stopper 30A abuts against the upper surface of the flange 4c or the outer surface of the neck 4a and prevents the bottle 4 from being further tilted. Therefore, the bottle 4 is prevented from wobbling under centrifugal forces when it is fed at a high speed or when it is reversed.

An example of an application wherein neck grippers 2 are used in an electron beam sterilization apparatus will be described below with reference to FIG. 4. The neck grippers 2 are disposed on a vessel feeding means 34 installed in a sterilization chamber 32 made up of walls of lead. The vessel feeding means 34 includes two sprockets 34a, 34b and an endless feed belt 34c trained around the sprockets 34a, 34b. The gripper 2 are mounted on the endless feed belt 34c at equal intervals. The neck grippers 2 are mounted on the endless feed belt 34c as pairs of two upper and lower grippers which are oriented in opposite directions. The two grippers in each pair grip the respective necks 4a of bottles 4 of resin, and feed one of the bottles 4 in a normal vertical state and the other in an inverted vertical state. The net grippers 2 in each pair are inverted at an inverting position A on a straight path extending from one of the sprockets (the right sprocket 34b in FIG. 4) toward the other sprocket 34a, vertically switching around the two bottles 4.

The grippers 2 of the vessel feeding means 34 are supplied with bottles 4 from outside of the sterilization chamber 32 through a supply wheel 36 that is disposed at the inlet of the chamber 32. The bottles 4 are sterilized by being irradiated with an electron beam emitted from an electron beam irradiation apparatus to be described below. After being sterilized, the bottles 4 are discharged from the sterilized chamber 32 through a discharge wheel 38. A supply position for supplying the bottles 4 from the supply wheel 36 to the vessel feeding means 34 is indicated by reference character B, and a discharge position for discharging the bottles 4 from the vessel feeding means 34 to the discharge wheel 38 is indicated by reference character C.

An electron beam irradiation apparatus 40 is disposed on a side of the sterilization chamber 32. The sterilization chamber 32 has an opening 32a defined in a wall thereof, and the electron beam irradiation apparatus 40 has an irradiation surface 40a disposed in the opening 32a. A thin foil of titanium or the like is attached to the irradiation surface 40a, which emits an electron beam through the foil. In the present embodiment, a region in front of the irradiation surface 40a to which the titanium foil is attached serves as an irradiation region D of the electron beam irradiation apparatus 40. An electron beam irradiation chamber 42 is defined around the irradiation region D. When a gripper 2 holding a bottle 4 passes through the electron beam irradiation chamber 42, the gripper 2 is irradiated with the electron beam from the electron beam irradiation apparatus 40. The direction in which the gripper 2 is irradiated with the electron beam is indicated by the arrows E in FIGS. 3 and 4.

Operation of the neck grippers 2 of the above structure as it is used in the electron beam sterilization apparatus will be described below. When a gripper 2 on the vessel feeding means 34 reaches the vessel supply position B, the gripper 2 is supplied with a bottle 4 from the supply wheel 36. As the gripper 2 moves on, the bottle 4 is pressed against the slanted surfaces 24Ac, 24Bc on the distal ends of the abutments 24A, 24B. The grips 10A, 10B are spread apart from each other, allowing the bottle 4 to move beyond the distal-end protrusions 24Aa, 24Ba between the slanted surfaces 24Ac, 24Bc on the distal ends and the arcuate surfaces, and enter between the arcuate surfaces. Thereafter, the grips 10A, 10B are returned under the repulsive forces from the leaf springs 12A, 12B and the springs 20A, 20B, holding the neck 4a of the bottle 4 between the arcuate surfaces. At this time, the arcuate surfaces do not contact the neck 4a of the bottle 4, but the distal-end protrusions 24Aa, 24Ba and the proximal-end protrusions 24Ab, 24Bb of the abutments 24A, 24B abut against the neck 4a of the bottle 4. As a result, since the area in which the abutments 24A, 24B are held in contact with the neck 4a is small, the portion of the bottle 4 which is not irradiated with the electron beam is minimized, and at the same time the bottle 4 is held stably.

The gripper 2 feeds the bottle 4 to a position in front of the irradiation surface 40a of the electron beam irradiation apparatus 40 while holding the neck 4a of the bottle 4. At this time, the distal end portion of the gripper 2 is directed toward the irradiation surface 40a, and is irradiated with the electron beam in the direction indicated by the arrows E in front of the irradiation surface 40a. At this time, the gripper 2 has such a posture that its supports 22A, 22B face in the feeding direction (see the arrow F in FIG. 3) which is perpendicular to the direction E in which the gripper 2 is irradiated with the electron beam. Consequently, the surfaces 22Aa, 22Ba which face each other lie substantially parallel to the direction E in which the gripper 2 is irradiated with the electron beam, and hence does not block the electron beam but allows the electron beam to pass behind the bottle 4. Inasmuch as the plates 26A, 28A, 26B, 28B lie substantially horizontally and substantially parallel to the direction E in which the gripper 2 is irradiated with the electron beam, the electron beam is not blocked by the upper and lower surfaces of the plates 26A, 28A, 26B, 28B. The bottle 4 held by the neck gripper 2 is thus sterilized by being irradiated with the electron beam. After each bottle 4 is irradiated with the electron beam for the first time, the bottle 4 is inverted in the inverting position A and then fed to the irradiation region D in front of the irradiation surface 40a, wherein the bottle 4 is irradiated with the electron beam for the second time in the opposite direction, so that the entire outer circumferential surface of the bottle 4 is sterilized. After the sterilization is finished, the bottle 4 is transferred to the discharge wheel 38 at the discharge position C and is then discharged.

With conventional grippers (e.g., the gripper disclosed in Patent document 4), the portion thereof which is held in contact with the bottle needs to have a wide area for stably feeding the bottle. Therefore, the grippers tend to block the electron beam and prevent the bottle from being sufficiently sterilized. Furthermore, as the electron beam does not reach a region behind the portion of the bottle which is held in contact with the gripper, the bottle is liable to have a wide region which remains unsterilized. With the structure of the gripper 2 according to the present embodiment, however, since the abutments 24A, 24B comprise the two thin plates 26A, 26B, 28A, 28B, the electron beam passes through the gap between those plates. When the neck gripper 2 holds the bottle 4, the supports 22A, 22B are not held in contact with the outer surface of the bottle 4. Therefore, the electron beam travels behind the bottle 4 between the outer surface of the neck 4a and the surfaces of the supports 22A, 22b, thus sterilizing substantially the entire surface of the bottle 4.

Since the gripper 2 is constructed as described above, it can hold the bottle 4 reliably and feed the bottle 4 stably, and can feed the bottle 4 at a high speed. If the gripper 2 is applied to an electron beam sterilization apparatus and is irradiated with the electron beam, it allows a sufficient dose of electron beam to be applied for efficiently sterilizing the bottle 4. With the gripper 2 of the above structure, the leaf springs 12A, 12B and the springs 20A, 20B make up a holding mechanism. If the neck 4a of the bottle 4 can be inserted between the abutments 24A, 24B while causing the springs to flex, then even when the neck 4a is different in shape or size, the abutments 24A, 24B do not need to changed in type, but may be applicable to a wide range of bottles. Furthermore, since the bottle 4 is inverted and irradiated with the electron beam twice, the entire surface of the bottle 4 can be sterilized with only one electron beam sterilization apparatus being installed. In the present embodiment, the upper plates 26A, 26B of the abutments 24A, 24B have flat upper surfaces which may abut against the lower surface of the flange 4c on the neck 4a of the bottle 4. However, if the upper surfaces of the upper plates 26A, 26B have projections or steps for point-to-point or line-to-line contact with the lower surface of the flange 4c, then the area of contact between the abutments 24A, 24B and the bottle 4 may further be reduced for effectively irradiating the lower surface of the flange 4c with the electron beam. In the above embodiment, the two points on the distal and proximal ends of the abutments 24A, 24B are held in abutment against the neck 4a of the bottle 4. However, the abutting points are not limited to the two points, but may comprise a different number of points, such as three points or four points. Those abutting points are interconnected by a common arcuate surface provided by each of upper and lower plates. However, three or more plates may be employed, and the surface between the abutting points may not necessarily be of an arcuate shape, but may be other shapes. Moreover, abutments themselves may be independent abutments in the form of two or more discrete plates, each of the supports 22A, 22B may have a plurality of abutments arranged in the circumferential direction of the neck 4a. While the gripper is described as being applied to an electron beam sterilization apparatus in the above embodiment, the gripper is not necessarily limited to being applied to an electron beam sterilization apparatus, but is also applicable to an apparatus for sterilizing or otherwise processing a bottle by irradiating the bottle with a radiation such as ultraviolet rays, infrared rays, or the like, or other radiating mediums, or an apparatus for sterilizing, cleaning, or otherwise processing a bottle by applying steam, a gas, or a liquid to the bottle. The gripper applied to these apparatus is also as effective as it is applied the electron beam sterilization apparatus because the area of contact thereof with the bottle is small. The gripper is also applicable to other bottle processing apparatus which are constructed to feed the bottle by holding the bottle stably.

The invention claimed is:

1. In a gripper provided in a vessel feeding means for holding a neck of a bottle made of a resin by gripping opposite sides of the resin bottle neck and conveying the resin bottle to an irradiation region of an electron beam irradiation apparatus, the improvement comprising the gripper having first and second supports provided at opposite sides of the bottle neck, a first abutment disposed on the first support and a second abutment disposed on the second support for abutting against an outer circumferential surface of the bottle neck when holding the bottle, the first abutment comprising a first support body and a second support body which are vertically spaced from each other and the second abutment comprising a third support body and a fourth support body which are vertically spaced from each other, wherein when the gripper holds the resin bottle, the first and second supports are not in contact with the outer circumferential surface of the resin bottle neck and, during irradiation with an electron beam, the electron beam passes through gaps provided between the vertically spaced-apart support bodies.

2. A gripper according to claim 1, wherein said support bodies comprise thin plates, respectively.

3. A gripper according to claim 1, wherein at least one of said supports has a wobble stopper for preventing the bottle from wobbling.

4. A gripper according to claim 3, wherein said support bodies abut against a lower portion of a flange on the neck of the bottle, and said wobble stopper abuts against an upper portion of said flange.

5. A gripper according to claim claim 1, wherein said abutments abut against the neck of the bottle made of resin at a plurality of points which are located to be spaced apart in a circumferential direction of the neck.

6. A gripper according to, claim 1, wherein when the gripper holds the bottle in said irradiation region, the gripper has such a posture that said supports face in a feeding direction which is perpendicular to the direction in which the gripper is irradiated with the electron beam and the support bodies of said abutments lie substantially parallel to the direction in which the gripper is irradiated with the electron beam.

* * * * *